(12) United States Patent
Chen et al.

(10) Patent No.: US 12,702,526 B2
(45) Date of Patent: Aug. 11, 2026

(54) STRUCTURE AND METHOD OF SWITCHABLE MULTI-MODE DENTAL HANDPIECE

(71) Applicant: THREE-IN-ONE ENTERPRISES CO., LTD., New Taipei City (TW)

(72) Inventors: Yung-Hsiu Chen, New Taipei City (TW); Kao Hua Chen, New Taipei City (TW)

(73) Assignee: THREE-IN-ONE ENTERPRISES CO., LTD., New Taipei City (TW)

( * ) Notice: Subject to any disclaimer, the term of this patent is extended or adjusted under 35 U.S.C. 154(b) by 71 days.

(21) Appl. No.: 18/671,604

(22) Filed: May 22, 2024

(65) Prior Publication Data

US 2024/0398509 A1 Dec. 5, 2024

Related U.S. Application Data

(60) Provisional application No. 63/503,602, filed on May 22, 2023.

(51) Int. Cl.

| | |
|---|---|
| ***A61C 1/12*** | (2006.01) |
| ***A61B 1/247*** | (2006.01) |
| ***A61C 5/40*** | (2017.01) |

(52) U.S. Cl.
CPC ................ *A61C 1/12* (2013.01); *A61B 1/247* (2013.01); *A61C 5/40* (2017.02)

(58) Field of Classification Search
CPC .... A61C 1/10; A61C 1/12; A61C 1/18; A61C 1/185; A61C 1/188; A61C 5/40; A61C 5/44; A61B 1/24; A61B 1/247
See application file for complete search history.

*Primary Examiner* — Edward Moran
*Assistant Examiner* — Christine L Nelson
(74) *Attorney, Agent, or Firm* — MUNCY, GEISSLER, OLDS & LOWE, P.C.

(57) ABSTRACT

A switchable multi-mode dental handpiece structure and method, includes: a root canal mirror assembly with an image sensor for capturing external images; a flexible hose with one end connected to the image sensor; a rigid tube connected to the other end of the flexible hose; a root canal operation assembly, includes: a working head; a driving device connected to the working head for driving the working head, the driving device being operable to follow the rotational direction of a steering wheel; a connecting rod linking the steering wheel; a mode switching push handle, connected to the rigid tube and the connecting rod, for switching between various handpiece modes, such as a linkage mode, an individual operation mode, a storage mode, and an intraoral operation mode.

7 Claims, 7 Drawing Sheets

STRUCTURE AND METHOD OF SWITCHABLE MULTI-MODE DENTAL HANDPIECE

CROSS-REFERENCE TO RELATED APPLICATIONS

This Non-provisional application claims priority under 35 U.S.C. § 119 (a) on Patent Application No(s). [63/503,602] filed in American United States May 22 2023, the entire contents of which are hereby incorporated by reference.

FIELD OF THE INVENTION

This invention relates to a dental handpiece structure and method that can switch between multiple modes, particularly an apparatus with various modes that facilitates endodontic treatment for dentists.

BACKGROUND OF INVENTION

Traditional dental handpieces have some drawbacks. For instance, when using a dental drill handpiece, dentists can only observe the drilling operation either visually or with a mirror. This method requires the dentist to hold the dental drill handpiece in one hand and the mirror in the other, making endodontic treatment very inconvenient for the dentist.

Another approach is a dental handpiece combined with an imaging device. While this solves the problem of the dentist holding the dental drill handpiece in one hand and the mirror in the other, this method usually involves mounting the imaging device on the dental drill handpiece. As a result, it only allows observation of the drilling process and cannot provide a detailed view inside the root canal after drilling.

Existing technology for root canal scopes cannot extend further into the depths of the root canal for treatment, and the design of dental drill handpieces cannot fully utilize their functions. This invention aims to provide a telescopic root canal scope combined with a dental drill handpiece, allowing dentists to perform endodontic treatment more effectively.

SUMMARY OF THE INVENTION

This invention provides a dental handpiece structure and method that can switch between multiple modes, including various handpiece modes such as linked mode, individual operation mode, storage mode, and intraoral operation mode, to suit the diverse needs of dentists.

a dental handpiece capable of switching between multiple modes comprises: a root canal scope device, which includes an image sensor for capturing external images, a flexible tube connected to one end of the image sensor, a rigid tube connected to the other end of the flexible tube, a transmission line passing through the flexible tube and/or the rigid tube, and connecting to the image sensor; a root canal operation assembly, which includes a working head, a drive device connected to the working head to drive it, a steering wheel connected to the drive device, the axis of the steering wheel being fixed to the outer casing of the handpiece, the drive device rotating with the direction of the steering wheel, a connecting rod connecting the steering wheel, and the transmission line connecting the drive device; a mode switching handle connecting the rigid tube and the connecting rod, used for switching between various handpiece modes; a handpiece outer casing, housing the aforementioned modules; and a main unit, which includes a power device connected to an external power source and converts it into the operating voltage of the system; a display device telecommunicating with the power device, displaying images captured by the image sensor.

A dental handpiece structure and method capable of switching between multiple modes, where a linked mode operation method includes: a mode switching handle includes a handle surface connecting a connecting rod and a rigid tube; when the operator pushes the handle surface downward, the mode switching handle links with the rigid tube, pulling a flexible tube through the rigid tube, thereby retracting an image sensor indirectly back into the handpiece outer casing; conversely, the mode switching handle links with the connecting rod, causing the connecting rod to rotate a steering wheel, lifting a drive device and a working head connected to the steering wheel upward out of the handpiece outer casing. Furthermore, when the handle surface is pushed upward, the mode switching handle links with the connecting rod, causing the connecting rod to rotate the steering wheel, thereby folding down the drive device and the working head connected to the steering wheel, retracting the working head into the handpiece outer casing; conversely, the mode switching handle links with the rigid tube, pushing the flexible tube through the rigid tube, thereby extending the image sensor out of the handpiece outer casing.

A dental handpiece structure and method capable of switching between multiple modes, where an individual operation mode operation method includes: a mode switching handle includes first and second handle surfaces individually connecting a rigid tube and a connecting rod; when the operator pushes the first handle surface downward, it links with the rigid tube, pulling a flexible tube through the rigid tube, thereby retracting an image sensor indirectly back into the handpiece outer casing; when the first handle surface is pushed upward, it links with the rigid tube, pushing the flexible tube through the rigid tube, thereby extending the image sensor out of the handpiece outer casing. Furthermore, when the operator pushes the second handle surface downward, it links with the connecting rod, causing the connecting rod to rotate a steering wheel, lifting a drive device and a working head connected to the steering wheel upward. When the second handle surface is pushed upward, it links with the connecting rod, causing the connecting rod to rotate the steering wheel, thereby folding down the drive device and the working head connected to the steering wheel, retracting the working head into the handpiece outer casing.

A dental handpiece structure and method capable of switching between multiple modes, where a storage mode involves retracting both the image sensor and the working head into the handpiece outer casing simultaneously using the first and second handle surfaces.

A dental handpiece structure and method capable of switching between multiple modes, where an intraoral operation mode operation method includes: a root canal operation assembly includes a working head, one end of a telescopic device connected to the working head, a drive device driving a transmission belt through the telescopic device to drive the working head; a gear connecting the telescopic device, with the gear axis fixed to the handpiece outer casing, allowing the telescopic device to move forward and backward as the gear rotates, and a connecting rod connecting the gear. Furthermore, when the operator pushes the handle surface downward, it links with the connecting rod, causing the gear to rotate, moving the telescopic device backward, indirectly retracting the working head into the handpiece outer casing; when the operator pushes the handle surface upward, it links with the connecting rod, causing the gear to rotate, moving the telescopic device forward, indirectly extending the working head out of the handpiece outer casing.

DETAILED DESCRIPTION OF THE INVENTION

The following description and explanation of the technical solution of the embodiments of the present invention are based on the accompanying drawings, which illustrate preferred embodiments of the present invention but not all possible embodiments. It should be noted that the drawings are for illustrative purposes only and do not represent the actual dimensions or positions of the components, nor are they intended to limit the scope of the present invention.

In the present invention, unless otherwise explicitly specified and limited, terms such as "installation," "setting up," "connecting," "fixing," etc., should be broadly interpreted. For example, it can refer to fixed connections or detachable connections, integral connections; mechanical connections or electrical connections; direct connections or indirect connections through intermediate media; connections within the components themselves. Ordinary skilled artisans in the field can understand the specific meanings of the above terms in the present invention according to the specific circumstances.

Figure 1:
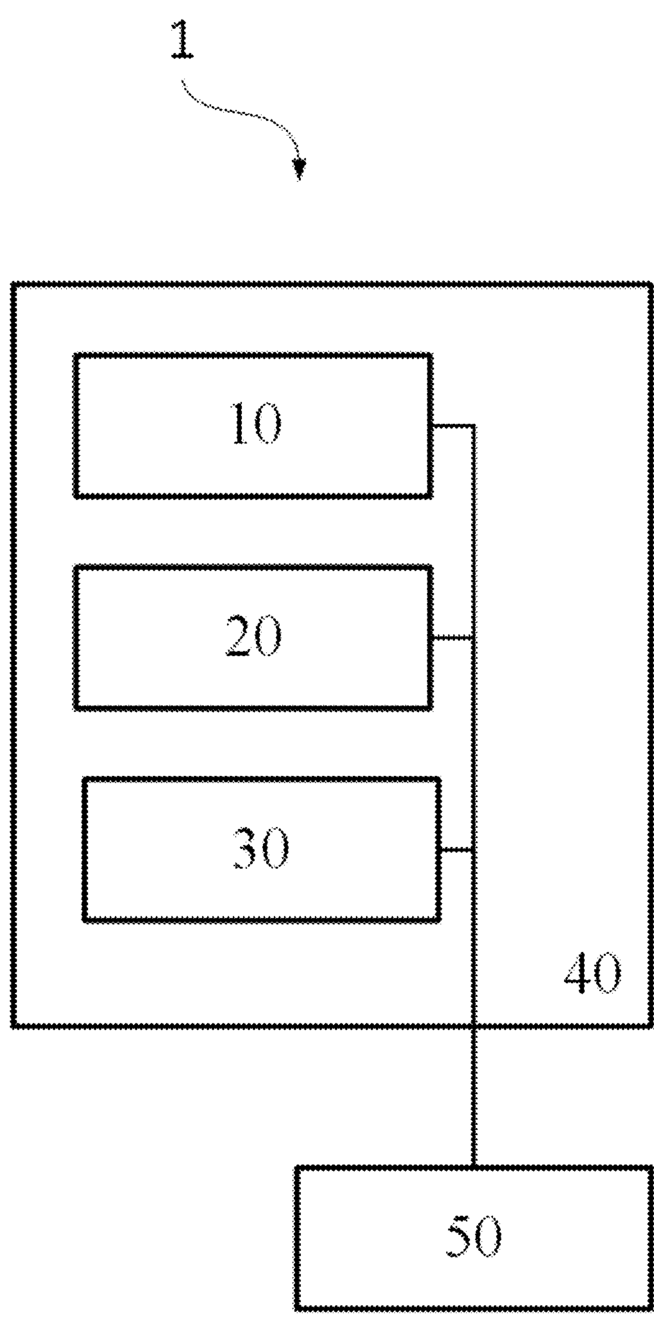
FIG. 1 shows a schematic diagram of switchable multi-mode dental handpiece.

Please refer to FIG. 1, which is a schematic diagram of one embodiment of the switchable multi-mode dental handpiece structure of the present invention. One embodiment of a switchable multi-mode dental handpiece 1 includes: a root canal mirror assembly 10, a root canal operation assembly 20, a mode switching push handle 30, a handpiece housing 40, a main unit 50 (not shown in the figure), and a transmission line (not shown in the figure).

Figure 2:
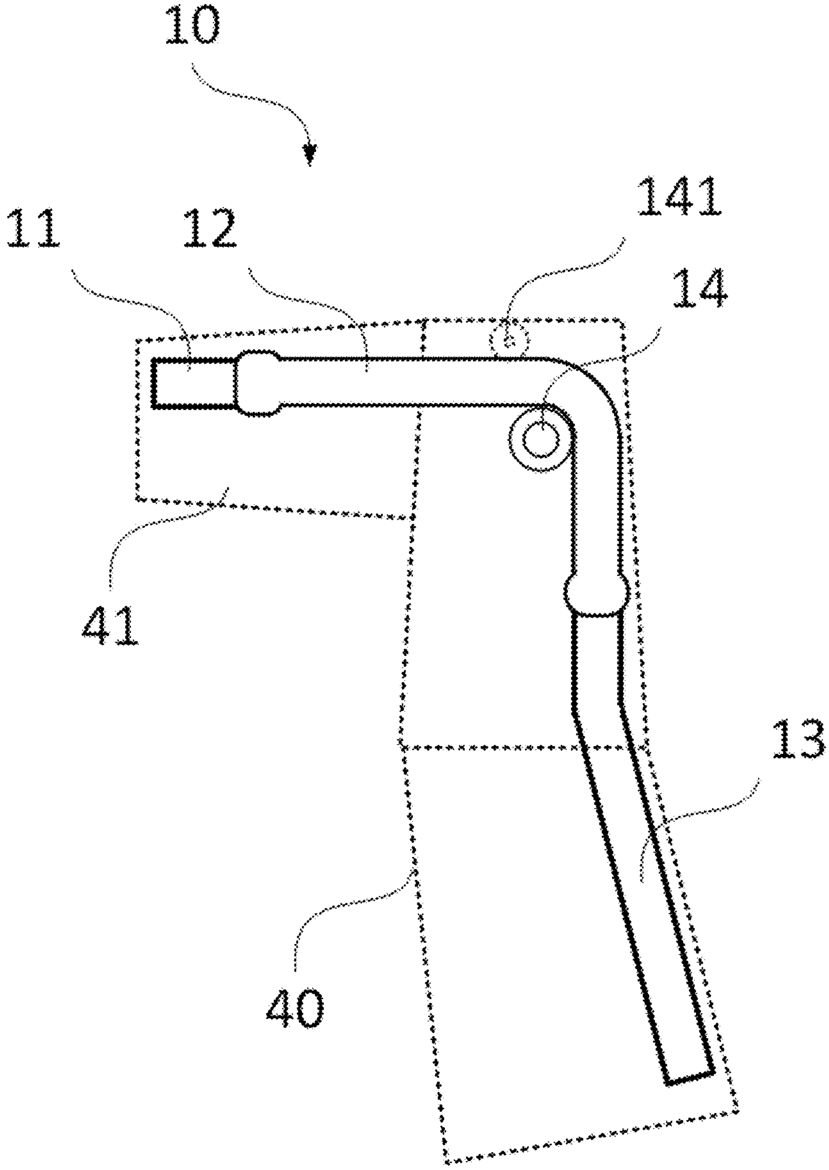
FIG. 2 shows a schematic diagram of root canal mirror assembly of switchable multi-mode dental handpiece.

Please refer to FIG. 2. The root canal mirror assembly 10 comprises: an image sensor (not shown in the figure) enclosed by an image sensor housing 11, which is located inside a handpiece head portion 41 of the handpiece housing 40; a flexible hose 12 connected to one end of the image sensor housing 11, with the inner diameter of the flexible hose 12 slightly smaller than the outer diameter of the image sensor housing 11; a rigid tube 13 connected to the other end of the flexible hose 12, with the outer diameter of the rigid tube 13 slightly larger than the inner diameter of the flexible hose 12; a roller 14, with its bearing fixed to the handpiece housing 40, allowing the flexible hose 12 to slide using the roller 14; the transmission line passes through the flexible hose 12 and the rigid tube 13, connecting the image sensor to the main unit 50, for transmitting an image signal from the image sensor and/or providing power to the image sensor.

Figure 3:
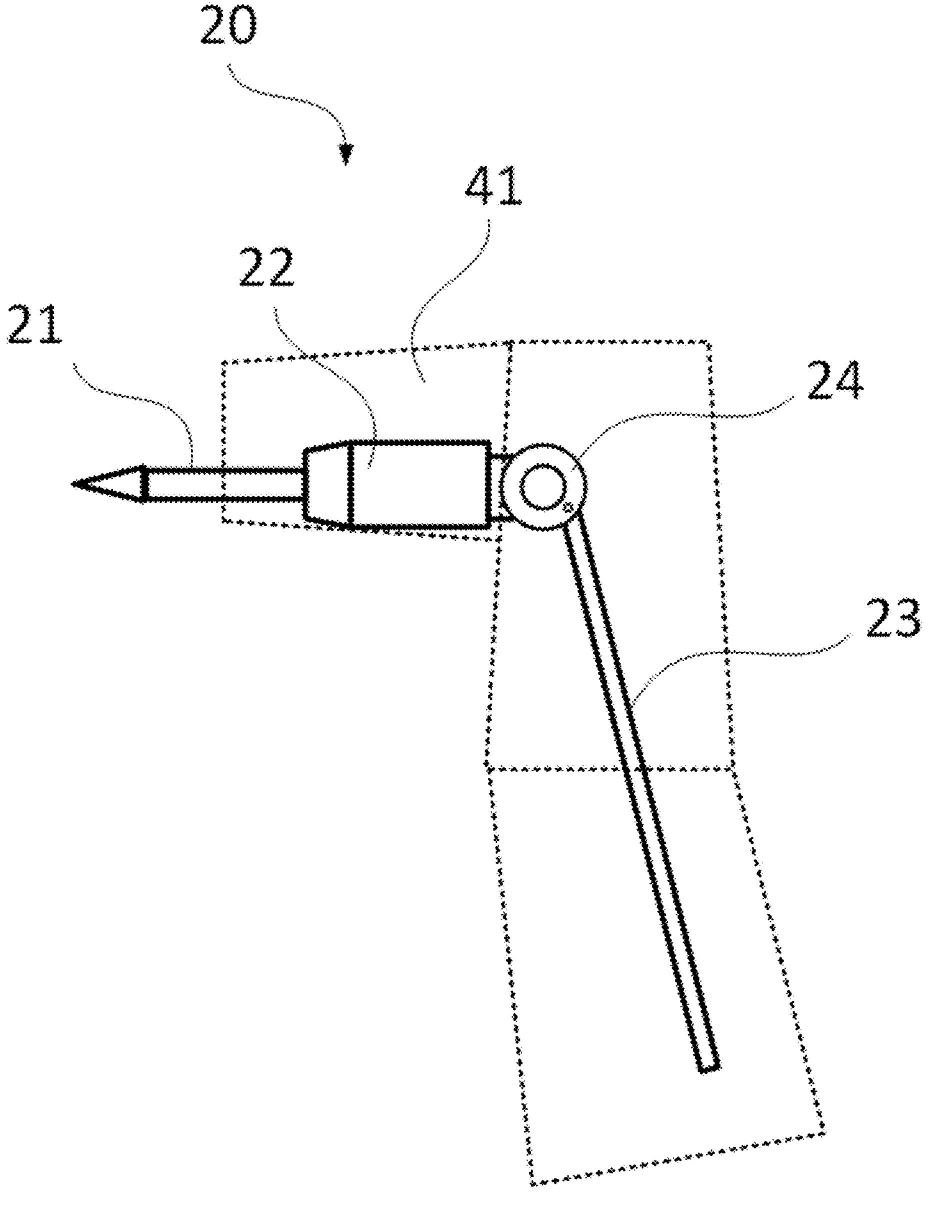
FIG. 3 shows a schematic diagram of root canal operation assembly of switchable multi-mode dental handpiece.

Please refer to FIG. 3. The root canal operation assembly 20 includes: a driving device 22 connected to a working head 21, with the driving device 22 located inside the handpiece head portion 41 of the handpiece housing 40, a steering wheel 24 connected to the driving device 22, with the bearing of the steering wheel 24 fixed to the handpiece housing 40, the driving device 22 extends the working head 21 out of the handpiece head portion 41 externally as the steering wheel 24 rotates, a connecting rod 23 connected to the steering wheel 24; the transmission line connects the driving device 22 to the main unit 50, and the main unit 50 provides power to the driving device 22.

Figure 4:
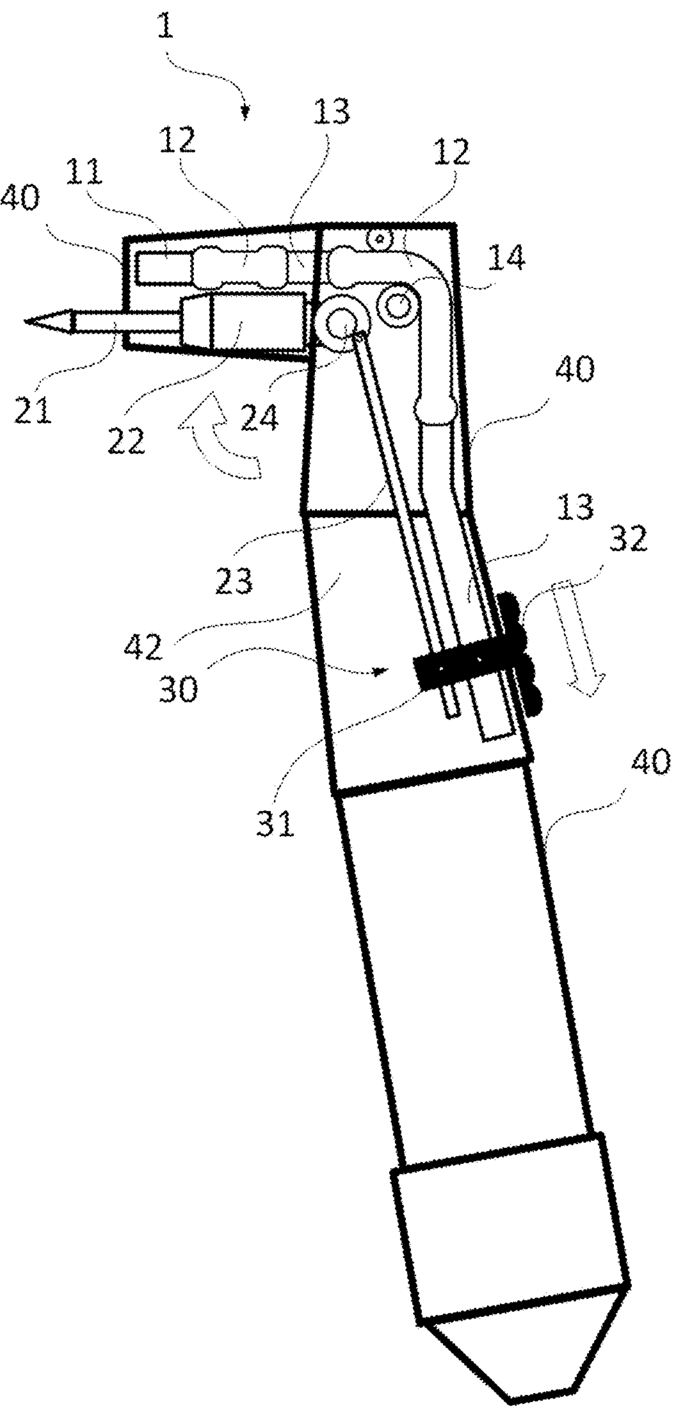
FIG. 4 shows a schematic diagram of working head usage state of switchable multi-mode dental handpiece.

Please refer to FIG. 4. a push handle connecting portion 31 of the mode switching push handle 30 is located inside a handpiece grip portion 42 of the handpiece housing 40, connecting the rigid tube 13 and the connecting rod 23; a push handle surface 32 of the mode switching push handle 30 is located outside the handpiece grip portion 42, used to switch between various modes of the switchable multi-mode dental handpiece 1.

The handpiece housing 40 comprises the handpiece head portion 41 and the handpiece grip portion 42, within which the root canal mirror assembly 10, the root canal operation assembly 20, and the mode switching push handle 30 are installed. The transmission line connects the handpiece housing 40 to the main unit 50. The operator can hold the handpiece grip portion 42 to use the switchable multi-mode dental handpiece 1.

The main unit 50 includes: a power supply device, which connects to an external power source and converts it to the operating voltage for the system; a display device with electrical connections to the power supply device, which displays images captured by the image sensor; a control panel with electrical connections to the display device, allowing adjustment of various parameters including zoom in/out, brightness adjustment, marking, and screen settings displayed by the display device; a processor with electrical connections to the control panel, executing the settings from the control panel, and additionally featuring analog-to-digital and digital-to-analog conversion functionalities (AD/DA); a storage device with electrical connections to the processor, which stores and records environmental image information.

The transmission line comprises a first signal line, which is electrically connected at one end to the power supply device and at the other end to either the image sensor or/and the driving device 22; and a second signal line, which is electrically connected at one end to the processor and at the other end to the image sensor housing 11.

When the root canal mirror assembly 10 is in use, the image sensor housing 11 extends outside the handpiece head portion 41, or when the root canal operation assembly 20 is in use, the working head 21 flips out from the handpiece head portion 41.

Ideally, the outer diameter of the image sensor housing 11 is smaller than or equal to 1.05 mm, and its length can be, but is not limited to, 7 mm.

The image sensor includes an endoscope, an electronic lens, a lens, and an optical fiber LED assembly.

In one embodiment, both ends of the flexible hose 12 connecting the image sensor housing 11 and the rigid tube 13 are equipped with inner raised rings on their inner edges. The outer edge of one end of the flexible hose 12 connecting the image sensor housing 11 and the rigid tube 13 has an outer raised ring. These inner and outer raised rings ensure a tight connection between the flexible hose 12 and the image sensor housing 11 and the rigid tube 13.

In one embodiment, the inner diameter of the flexible hose 12 is equal to the outer diameter of both the image sensor housing 11 and the rigid tube 13.

The connection methods between the flexible hose 12 and the rigid tube 13 include socket press-fit, heat bonding, ultrasonic bonding, high-frequency bonding, dual-material adhesion methods, and dental-grade epoxy bonding, among others.

In one embodiment, the roller 14 can be replaced by positioning pillars, positioning plates, or tracks, and the flexible hose 12 can slide using positioning pillars or positioning plates.

Ideally, the handpiece housing 40 also includes an auxiliary wheel 141 corresponding to the roller 14 installation. The flexible hose 12 can slide using both the roller 14 and the auxiliary wheel 141.

The working head 21 can be equipped with various tools required for dental treatment, including dental drills, cleaning heads, etc. It can accommodate a variety of working heads for dental treatment.

One embodiment of a switchable multi-mode dental handpiece structure comprising: a root canal mirror assembly 10 comprising, an image sensor for capturing external images, and a flexible hose 12 connected at one end to the image sensor and at the other end to a rigid tube 13, wherein pushing or pulling the rigid tube 13 actuates extension or retraction of the image sensor within a handpiece housing 40, and a transmission line traversing the flexible hose 12 and the rigid tube 13 and connecting to the image sensor; a root canal operation assembly 20 comprising, a working head 21 mounted on a driving device 22, a steering wheel 24 connected to the driving device 22 and fixed within the handpiece housing 40 using bearings, a connecting rod 23 connecting the steering wheel 24 for altering the angle of the steering wheel 24, wherein the direction of the working head 21 changes with the angle of the steering wheel 24, and the transmission line connecting to the driving device 22; and at least one mode switching push handle 30 installed on the handpiece housing 40 and slidable thereon, wherein the mode switching push handle 30 is connected to the rigid tube 13 and the connecting rod 23, and pushing or pulling the mode switching push handle 30 downward or upward actuates extension or retraction of the image sensor and/or the working head 21 within the handpiece housing 40.

In the above, the root canal mirror assembly 10 further comprises an image sensor housing 11 enclosing the image sensor, the image sensor housing 11 being connected at one end to the flexible hose 12 and having a light-transmitting portion at the other end.

In one usage state of the linkage mode in the switchable multi-mode dental handpiece method, please refer to FIG. 4. The method includes: a mode switching push handle 30 includes a push handle surface 32 connected to a connecting rod 23 and a rigid tube 13. When the operator pushes down the push handle surface 32, the mode switching push handle 30 actuates the rigid tube 13, pulling a flexible hose 12 and assisting its movement using a roller 14, indirectly retracting an image sensor housing 11 into a handpiece head portion 41 of a handpiece housing 40. At the same time, the mode switching push handle 30 actuates the connecting rod 23, causing clockwise rotation of a steering wheel 24 connected to it, lifting up a driving device 22 and a working head 21 attached to the steering wheel 24, positioning the working head 21 outside the handpiece head portion 41.

Figure 5:
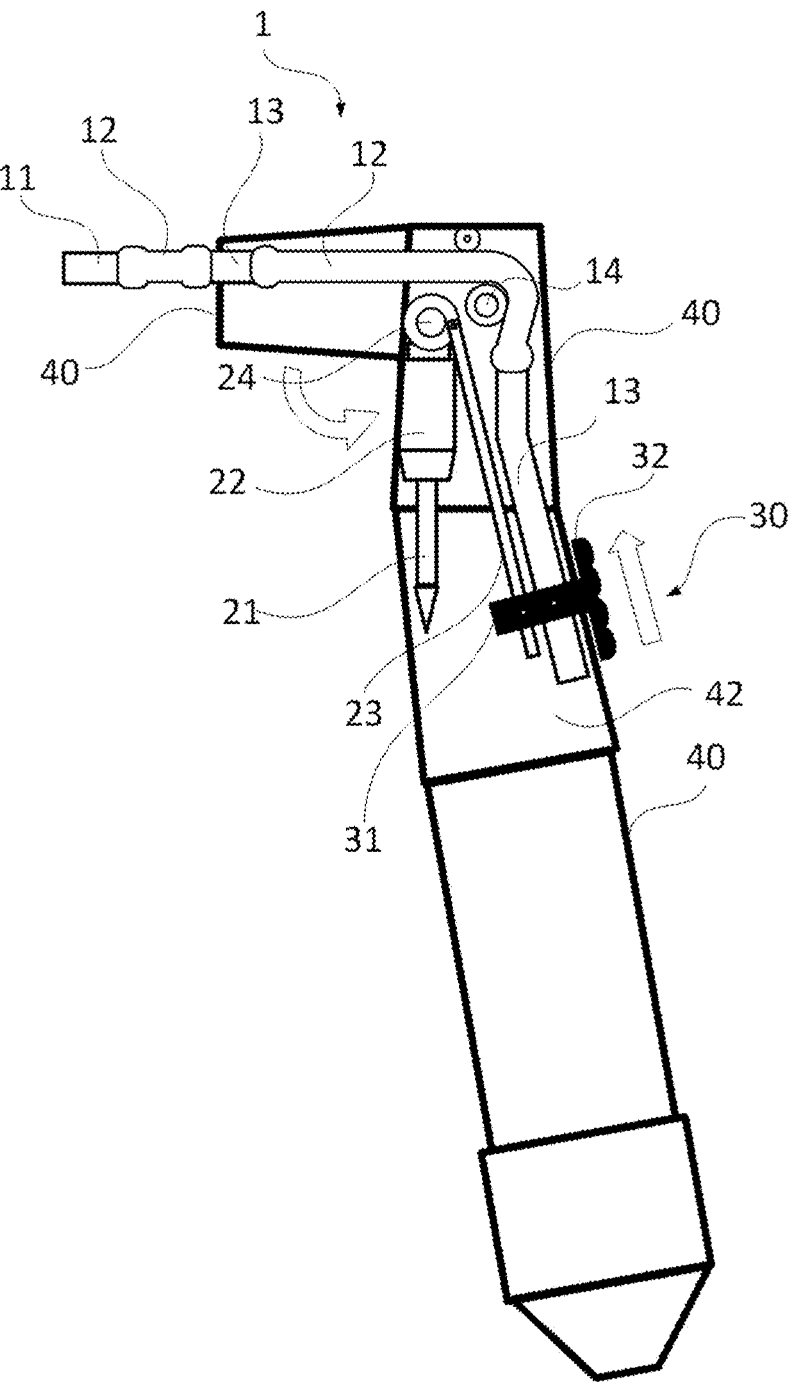
FIG. 5 shows a schematic diagram of root canal mirror usage state of switchable multi-mode dental handpiece.

In one embodiment of the present invention, in the root canal mirror usage state of the linkage mode in the switchable multi-mode dental handpiece structure and method, please refer to FIG. 5. The method includes: when the Push handle surface 32 of the mode switching push handle 30 are pushed upward, the mode switching push handle 30 actuates the connecting rod 23, causing counterclockwise rotation of the steering wheel 24 connected to it. This action causes the driving device 22 and the working head 21 attached to the steering wheel 24 to fold downwards, retracting the working head 21 into the handpiece housing 40. Conversely, the mode switching push handle 30 actuates the rigid tube 13, pushing the flexible hose 12, and assisting its movement using the roller 14, thereby extending the image sensor housing 11 outside the handpiece head portion 41 of the handpiece housing 40.

The handpiece housing 40 includes a housing opening along the path of upward flipping and downward folding of the working head 21 and the driving device 22.

In addition, on the housing opening, an active plate and a spring are further installed. The active plate closes after the working head 21 and the driving device 22 have passed through.

In the mentioned linkage mode, the ability to switch between multiple modes allows the driving device 22 and the working head 21 to fold up and/or fold down outside the oral cavity during operation.

The material of the flexible hose 12 includes elastic rubber tubing and silicone tubing.

The material of the rigid tube 13 includes ABS plastic and stainless steel.

Figures 6A, 6B:
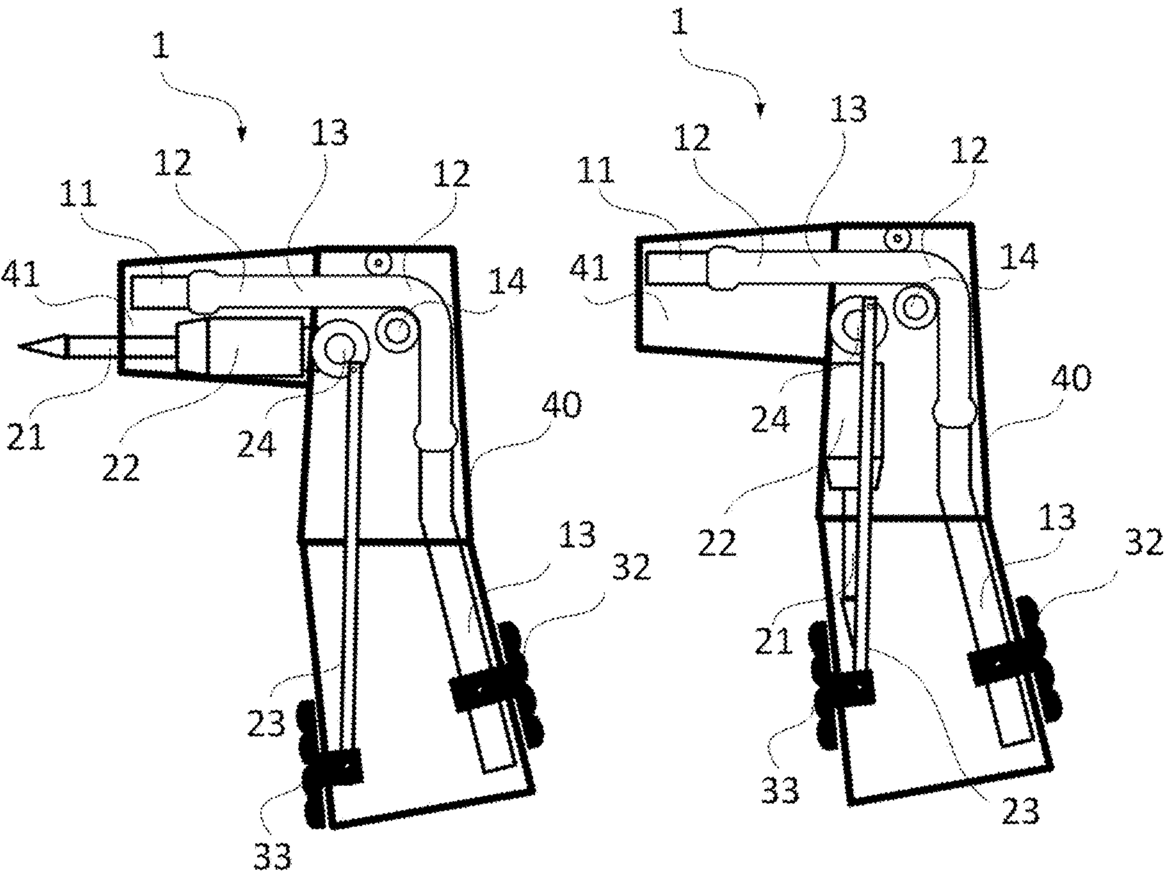
FIGS. 6A and 6B show schematic diagram of individual operating modes of switchable multi-mode dental handpiece.

In one embodiment of the present invention, in the individual operation mode of the switchable multi-mode dental handpiece method, please refer to FIGS. 6A and 6B. The method includes: two mode switching push handles 30, each includes a push handle surface 32 and 33, individually connected to a rigid tube 13 and a connecting rod 23. When the push handle surface 32 are pushed downward, they actuate the rigid tube 13, pulling a flexible hose 12 and assisting its movement using a roller 14, thereby retracting an image sensor housing 11 into a handpiece housing 40 of a handpiece head portion 41. When the push handle surface 32 are pushed upward, they actuate the rigid tube 13, pushing the flexible hose 12 and extending the image sensor housing 11 outside the handpiece head portion 41.

In the mentioned scenario, when the operator pushes the push handle surface 33 downward, they actuate the connecting rod 23, causing clockwise rotation of a steering wheel 24. This action lifts up a driving device 22 and a working head 21 attached to the steering wheel 24 through a housing opening in the handpiece housing 40. When the push handle surface 33 are pushed upward, they actuate the connecting rod 23, causing counterclockwise rotation of the steering wheel 24. This action folds down the driving device 22 and the working head 21 through the housing opening in the handpiece housing 40, retracting the working head 21 into the handpiece housing 40.

In one embodiment, the switchable multi-mode dental handpiece structure and method include a storage mode, as shown in FIG. 6B. This method involves retracting the image sensor housing 11 and the working head 21 into the handpiece housing 40 using the Push handle surface 32 and 33.

In one embodiment, a method for a operation method of switchable multi-mode dental handpiece, comprising: pushing downward or upward at least one mode switching push handle 30 mounted on a handpiece housing 40, wherein the mode switching push handle 30 actuates a connecting rod 23 which rotates a steering wheel 24; causing a driving device 22 and a working head 21 connected to the steering wheel 24 to flip upward or fold downward through a housing opening to a handpiece head portion 41 or retract into the handpiece housing 40; wherein, during the pushing downward or upward of the mode switching push handle 30, the mode switching push handle indirectly pulls or extends a flexible hose 12 by pulling a rigid tube 13, thereby retracting or extending an image sensor into or out of the handpiece housing 40.

Figures 7A, 7B:
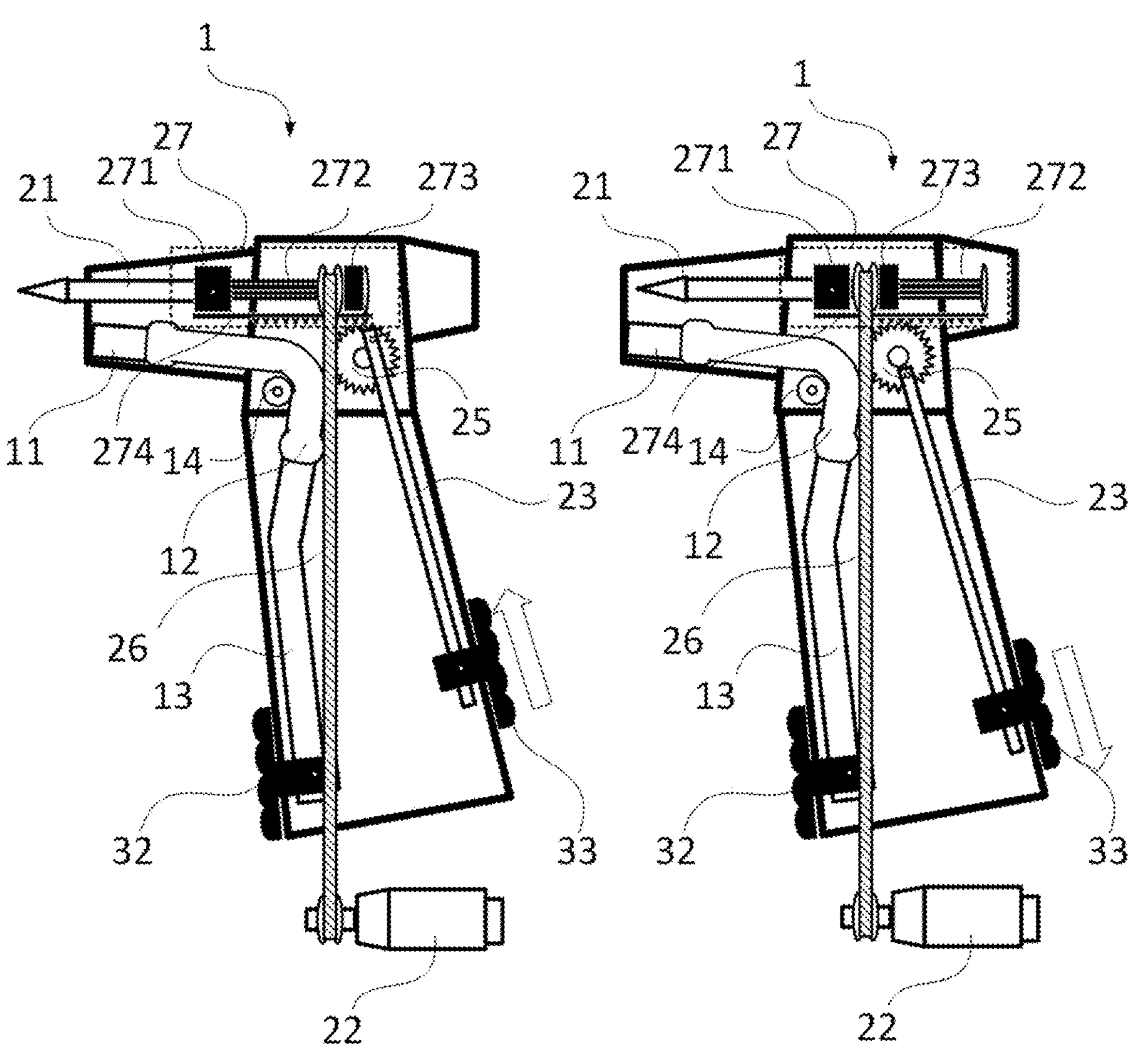
FIGS. 7A and 7B show schematic diagram of intraoral operation mode of switchable multi-mode dental handpiece.

In one embodiment, a method for the intraoral operation mode of the switchable multi-mode dental handpiece, please refer to FIGS. 7A and 7B. The method includes: a root canal operation assembly 20 includes: a working head 21, which is a tool necessary for dental treatment; a telescoping device 27 connected at one end to the working head 21; a driving device 22 rotating the telescoping device 27 via a transmission belt 26, indirectly causing the working head 21 to rotate; a gear 25 connecting to the telescoping device 27, fixed to a handpiece housing 40 by a gear bearing, allowing the telescoping device 27 to move back and forth as the gear 25 rotates; and a connecting rod 23 connecting to the gear 25.

In the mentioned scenario, when the operator pushes a push handle surface 33 downward, they actuate the connecting rod 23, causing clockwise rotation of the gear 25. This action moves the telescoping device 27 backward, indirectly retracting the working head 21 into the handpiece housing 40. When the Push handle surface 33 are pushed upward, they actuate the connecting rod 23, causing counterclockwise rotation of the gear 25. This action moves the telescoping device 27 forward, indirectly extending the working head 21 outside the handpiece housing 40. The intraoral operation mode allows for operation within the oral cavity.

In one embodiment, a switchable multi-mode dental handpiece comprising: a working head 21 connected to a telescoping device 27, with a driving device 22 driving the telescoping device 27 to rotate through a transmission belt 26, thereby indirectly causing the working head 21 to rotate; a gear 25 fixed to a handpiece housing 40 via a gear bearing and connected to the telescoping device 27, with the telescoping device 27 moving back and forth with the rotation of the gear 25; a mode switching push handle 30 mounted on the handpiece housing 40 and slidable along the handpiece housing 40, the mode switching push handle 30 moving up or down to link a connecting rod 23 to rotate the gear 25, causing the telescoping device 27 to move backward or forward, thereby indirectly causing the working head 21 to retract or extend from the handpiece housing 40; an image sensor for capturing external images, with a flexible hose 12 connected at one end to the image sensor and at the other end to a rigid tube 13, wherein the mode switching push handle 30 moving up or down to link the rigid tube 13 to push or pull the flexible hose 12, causing the image sensor to extend or retract from the handpiece housing 40; and a transmission line running through the flexible hose 12 and the rigid tube 13 and connected to the image sensor.

In one embodiment, the telescoping device 27 comprises: a working head buckle 271, capable of accommodating tools required for dental treatment to replace the working head 21. a gear rod 274 connected at one end to the working head buckle 271. The other end has multiple serrations that engage with the gear 25. Rotation of the gear 25 clockwise or counterclockwise can drive the gear rod 274 to move back and forth. a rotating rod 272 connected at one end to the working head buckle 271. The transmission belt 26 can drive the rotating rod 272 to rotate, indirectly rotating the working head 21. A double-layer ring 273, the outer layer is fixed to the handpiece housing 40, and the inner layer allows the rotating rod 272 to pass through and slide within it. Both the inner and outer layers of the double-layer ring 273 are rotatable.

In the described scenario, please refer to FIGS. 7A and 7B. When the operator pushes the Push handle surface 33 downward, it actuates the connecting rod 23, causing clockwise rotation of the gear 25. This movement drives the gear rod 274, engaged with the gear 25, to move backward, thereby moving the working head buckle 271 and the working head 21 backward. When the operator pushes the Push handle surface 33 upward, it actuates the connecting rod 23, causing counterclockwise rotation of the gear 25. This movement drives the gear rod 274 to move forward, thereby moving the working head buckle 271 and the working head 21 forward. The rotating rod 272 can move relative to the double-layer ring 273.

In one embodiment, the rotating rod 272 includes a cross-shaped rod, a star-shaped rod, and a serrated rod. The inner shape of the double-layer ring 273 corresponds to the shape of the rotating rod 272.

In one embodiment of the intraoral operation mode, the driving device 22 can be positioned at the end of the handpiece grip. It indirectly rotates the working head 21 through the transmission belt 26.

In one embodiment, the mode switching push handle 30 comprises an electronic type, consisting of a motor and buttons for mode switching.

The root canal mirror assembly 10 further comprises a plurality of flexible hose 12, each correspondingly connected to a plurality of rigid tubes 13.

In one embodiment, please refer to FIG. 4. The root canal mirror assembly 10 further includes: multiple flexible hoses and multiple rigid tubes. The image sensor housing 11 is connected to one end of a first flexible hose, and the other end is connected to one end of a first rigid tube. The other end of the first rigid tube is connected to one end of a second flexible hose, and the other end is connected to one end of a second rigid tube. The other end of the second rigid tube is connected to the mode switching push handle 30.

The size of the image sensor housing 11 allows it to penetrate deep into the patient's teeth. It can bend along the curvature of the root canal walls, making it easier for the image sensor housing 11 to approach the root canal to obtain root canal imaging information.

In one embodiment, the root canal mirror assembly 10 further includes a lighting device located within the space of the handpiece housing 40. This lighting device is connected to the first signal line of the transmission line and is powered by the power supply device. Additionally, there are multiple optical fibers within the internal space of the handpiece housing 40, connecting to the lighting device. These optical fibers utilize the principle of total internal reflection to transmit the light emitted by the lighting device to the front end of the image sensor housing 11. These optical fibers are also known as fiber optic cables or optical fibers.

There is a space between the image sensor housing 11 and the image sensor, and the optical fibers are distributed within this space.

The invention claimed is:

1. A switchable multi-mode dental handpiece comprising:

a root canal mirror assembly comprising, an image sensor for capturing external images, and a flexible hose connected at one end to the image sensor and at the other end to a rigid tube, wherein pushing or pulling the rigid tube actuates extension or retraction of the image sensor within a handpiece housing, and a transmission line traversing the flexible hose and the rigid tube and connecting to the image sensor;

a root canal operation assembly comprising, a working head mounted on a driving device, a steering wheel connected to the driving device and fixed within the handpiece housing using bearings, a connecting rod connecting the steering wheel for altering the angle of the steering wheel, wherein the direction of the working head changes with the angle of the steering wheel, and the transmission line connecting to the driving device; and at least one mode switching push handle installed on the handpiece housing and slidable thereon, wherein the mode switching push handle is connected to the rigid tube and the connecting rod, and pushing or pulling the mode switching push handle downward or upward actuates extension or retraction of the image sensor and/or the working head within the handpiece housing.

2. The switchable multi-mode dental handpiece of claim 1, wherein the root canal mirror assembly further comprises a plurality of flexible hoses, each correspondingly connected to a plurality of rigid tubes.

3. The switchable multi-mode dental handpiece of claim 1, wherein the root canal mirror assembly further comprises an image sensor housing enclosing the image sensor, the image sensor housing being connected at one end to the flexible hose and having a light-transmitting portion at the other end.

4. The switchable multi-mode dental handpiece of claim 1, wherein the number of the at least one mode switching push handle is one, and when the mode switching push handle is pushed downward, the driving device and the working head flip upward while the image sensor retracts into the handpiece housing, and when the mode switching push handle is pushed upward, the driving device and the working head fold downward while the image sensor extends out of the handpiece housing.

5. An operation method of the switchable multi-mode dental handpiece according to claim 1, comprising:

pushing downward or upward the at least one mode switching push handle mounted on the handpiece housing, wherein the mode switching push handle actuates the connecting rod which rotates the steering wheel;

causing the driving device and the working head connected to the steering wheel to flip upward or fold downward through a housing opening to a handpiece head portion or retract into the handpiece housing;

wherein, during the pushing downward or upward of the mode switching push handle, the mode switching push handle indirectly pulls or extends the flexible hose by pulling the rigid tube, thereby retracting or extending the image sensor into or out of the handpiece housing.

6. The operation method of claim 5, wherein the number of the at least one mode switching push handle is one, and when the mode switching push handle is pushed downward, the driving device and the working head flip upward while the image sensor retracts into the handpiece housing, and when the mode switching push handle is pushed upward, the driving device and the working head fold downward while the image sensor extends out of the handpiece housing.

7. The operation method of claim 5, wherein the mode switching push handle comprises a first mode switching push handle for individually controlling extension and retraction of the image sensor at the handpiece head portion, and a second mode switching push handle for individually controlling upward and downward folding of the driving device and the working head.

* * * * *